US012590265B2

(12) United States Patent
Hölscher et al.

(10) Patent No.: US 12,590,265 B2
(45) Date of Patent: Mar. 31, 2026

(54) 1-NORBORNAN-2-YLPROPAN-2-ONE AS A FRAGRANCE

(71) Applicant: Symrise AG, Holzminden (DE)

(72) Inventors: Bernd Hölscher, Halle (DE); Marc Mansfeld, Brevörde (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 18/861,963

(22) PCT Filed: May 3, 2022

(86) PCT No.: PCT/EP2022/061834
§ 371 (c)(1),
(2) Date: Oct. 31, 2024

(87) PCT Pub. No.: WO2023/213382
PCT Pub. Date: Nov. 9, 2023

(65) Prior Publication Data
US 2025/0257283 A1 Aug. 14, 2025

(51) Int. Cl.
*C11B 9/00* (2006.01)
*A61K 8/35* (2006.01)
*A61Q 13/00* (2006.01)

(52) U.S. Cl.
CPC .............. *C11B 9/0015* (2013.01); *A61K 8/35* (2013.01); *A61Q 13/00* (2013.01)

(58) Field of Classification Search
None
See application file for complete search history.

(56) References Cited

U.S. PATENT DOCUMENTS

2013/0045906 A1* 2/2013 Birkbeck .............. C07C 49/115
510/105

* cited by examiner

*Primary Examiner* — Jessica Whiteley
(74) *Attorney, Agent, or Firm* — Timothy H. Van Dyke; Wolter Van Dyke Davis, PLLC

(57) ABSTRACT

Suggested is the use of 1-Norbornan-2-ylpropan-2-one as a fragrance.

12 Claims, No Drawings

1-NORBORNAN-2-YLPROPAN-2-ONE AS A FRAGRANCE

FIELD OF THE INVENTION

The present invention relates to the use of 1-Norbornan-2-ylpropan-2-one as a fragrance. Furthermore, the present invention relates to fragrance compositions, their use and a method for imparting, modifying and/or enhancing certain fragrance notes.

BACKGROUND OF THE INVENTION

On the part of the perfume industry, new fragrance creations are permanently needed. However, the creation of a new fragrance or fragrance compositions involves a number of challenges. For example, it is necessary to select a specific composition of a few fragrances from an almost unlimited number of possible structures known from the prior art, in order to satisfy a specific need of the market and provide a product that matches the specific profile required by the customer. Suitable fragrances show a very beneficial performance, but in combination with other fragrances may develop unpleasant and thus detrimental odor aspects, making it difficult or even impossible to use them for the specific purpose.

A second important problem concerns the need to provide fragrance compositions that are not only consistent with a particular odor profile, but also possess so-called secondary beneficial properties. Indeed, many fragrance compositions known from the market have significant drawbacks in use, such as poor solubility and stability to storage, but also failures in subjective issues such as richness, charisma, and the like. In addition, many known fragrance compositions require high dosages to achieve the desired odor result. Another requirement for fragrances today is high biodegradability as well as dermatological and toxicological safety. Consequently, there is a particularly high demand for providing fragrances that have a large effect on other fragrances even at small dosages and change rather unpleasant odor impressions into positive ones and/or enhance pleasant odor impressions.

Thus, the underlying problem of the present invention was to provide a new fragrance with the ability to enhance positive and beneficial fragrance aspects of other fragrances and/or (at the same time) to reduce, inhibit and/or mask undesirable unpleasant fragrance aspects. In particular, the new fragrance should also be characterized by improving the stability, solubility and overall performance of other fragrances, as well as reducing the required dosage. Finally, the fragrance compositions themselves should have excellent biodegradability and be harmless to humans and the environment.

DESCRIPTION OF THE INVENTION

This is solved by the use of 1-Norbornan-2-ylpropan-2-one as a fragrance.

1-Norbornan-2-ylpropan-2-one to be used according to the invention may be present in any stereoisomeric form or may be present as any mixture of stereoisomers.

What has been said herein for 1-Norbornan-2-ylpropan-2-one, in particular the advantages described herein, also apply to a mixture of stereoisomers of 1-Norbornan-2-ylpropan-2-one to be used or to be employed according to the invention.

1-Norbornan-2-ylpropan-2-one possesses olfactory properties which are quite unique and which clearly differ from and also surpass those of known odoriferous substances. The suitability of 1-Norbornan-2-ylpropan-2-one as a fragrance was previously unknown. It is therefore particularly surprising that in the already well-studied field a fragrance with valuable, interesting and complex olfactory properties could be found.

1-Norbornan-2-ylpropan-2-one has the following structural formula

Formula I

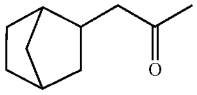

and, preferably, the following characteristic: Cas Nr.: 31683-73-5

As mentioned above, its suitability as a fragrance is not known. Likewise, no precise odor description is available, however, according to the inventors, 1-Norbornan-2-ylpropan-2-one smells fruity, towards isoamyl acetate and wintergreen.

Consequently, the inventors have made the surprising discovery that 1-Norbornan-2-ylpropan-2-one is suitable as a fragrance and, in small dosages, produces special effects in combination with pleasant smelling compounds, whereby these compounds are different from 1-Norbornan-2-ylpropan-2-one.

In a preferred embodiment according to the invention, 1-Norbornan-2-ylpropan-2-one is used for augmenting of one or more pleasant olfactory impression of one or more pleasant smelling compounds, whereby this compound/these compounds is/are different from 1-Norbornan-2-ylpropan-2-one. Preferably, the one or more pleasant olfactory impression of the one or more pleasant smelling compounds is selected from augmentation and/or improvement of the floweriness and/or naturalness, in particular more towards lavender. This means that 1-Norbornan-2-ylpropan-2-one preferably augments or improves the floweriness and/or the naturalness of pleasant smelling compounds. In particular, 1-Norbornan-2-ylpropan-2-one shifts the olfactory impression of these substances more towards lavender.

As used herein, the singular form “a,” “an,” and “the” include plural references unless the context clearly dictates otherwise. For example, the term “a compound” or “at least one compound” may include a plurality of compounds, including mixtures thereof. Also, the plural form include a singular embodiment, unless the context clearly dictates otherwise. For example, the term “one or more pleasant smelling compounds” also includes embodiment with only one pleasant smelling compound.

The fact that 1-Norbornan-2-ylpropan-2-one to be used according to the invention may impart a very complex and varied overall sensory impression, which can otherwise usually only be achieved by mixtures of several components (such as essential oils or spice mixtures), is particularly surprising.

Beyond the primary, namely olfactory, properties, 1-Norbornan-2-ylpropan-2-one additionally possesses positive secondary properties, in particular a high substantivity compared to fragrances with similar olfactory properties, as well as a high stability in certain media and preparations, a high extensibility, and is also biodegradable.

It is also recognized that 1-Norbornan-2-ylpropan-2-one can excellently function as a so-called booster (amplifier; enhancer). Preferably, 1-Norbornan-2-ylpropan-2-one is used as a booster for one or more pleasant olfactory impression of one or more pleasant smelling compounds, In other words: The use of 1-Norbornan-2-ylpropan-2-one together with other pleasant smelling compounds enhances their pleasant smelling odor notes.

Moreover, 1-Norbornan-2-ylpropan-2-one to be used according to the invention can enhance the intensity of a fragrance composition fragrance composition and round off the overall odor of the mixture. The compound described herein can therefore be used to impart more floweriness and/or naturalness to other compounds, especially to pleasant smelling compounds with at least one or more pleasant olfactory impression. Furthermore, 1-Norbornan-2-ylpropan-2-one is suitable as an agent for increasing the substantivity and/or retention of a fragrance composition.

"Pleasant smelling compounds" in the context of the present invention are generally to be understood as substances that evoke one or more pleasant odor impressions, be it as a primary or as a secondary/subordinate olfactory note. The term "pleasant smelling compounds" and "fragrances" are used interchangeably in the context of the present invention.

Preferably, said one, more or all pleasant smelling compounds different from 1-Norbornan-2-ylpropan-2-one are selected from the group consisting of fragrances having a molar mass within the range of from 150 g/mol to 285 g/mol, particularly alcohols, aldehydes, ketones, ethers, esters and carboxylates having a molar mass in the range of from 150 g/mol to 285 g/mol.

More preferably, said one, more or all pleasant smelling compounds are selected from the group consisting of 4-Methoxybenzaldehyde, Borneol, Isoborneol, 1-benzopyran-2-one, 2-Ethyl-3-hydroxy-4H-pyran-4-one, 3-Ethoxy-4-hydroxybenzaldehyde, 1,3,3-Trimethyl-2-oxabicyclo[2.2.2]octane, methyl 2,4-dihydroxy-3,6-dimethylbenzoate, trans-3,7-dimethyl-2,7-octadien-1-ol, Geraniol acetate, cis-3-Hexenylisovalerianat, hexyl acetate, hexyl butyrate, hexyl isobutyrate, 2-methyl-2-butenoic acid, hexyl ester, Bornan-2-on, lavandin, 3,7-Dimethylocta-1,6-dien-3-ol, 5-Methyl-2-(propan-2-yl)cyclohexan-1-ol, (2Z)-3,7-Dimethylocta-2,6-dien-1-ol, Nerol acetate, α: (3E)-3,7-Dimethylocta-1,3,7-triene, cis-β: (3Z)-3,7-Dimethylocta-1,3,6-triene, trans-β: (3E)-3,7-Dimethylocta-1,3,6-triene, 4-Methyl-1-(propan-2-yl)cyclohex-3-en-1-ol, p-Menth-1-en-8-ol, 2-(4-Methylcyclohex-3-en-1-yl)propan-2-ol, 4-Hydroxy-3-methoxybenzaldehyde.

In a preferred embodiment according to the present invention, the ratio of total mass of the pleasant smelling compound to the total mass of -(Methoxymethyl)-2-methylbenzene is in the range of 1 to 1000 to 1 to 100, preferably from 1 to 600 to 1 to 400.

1-Norbornan-2-ylpropan-2-one can be used in a variety of products; it can be used as a single fragrance, but it can be combined particularly advantageously with other pleasant smelling compounds, in particular fragrances in different proportions to form fragrance mixtures, and novel and original perfume compositions can also be created.

Accordingly, one aspect of the invention also relates to a fragrance mixture and possibly further constituents (solvents or the like), which contains 1-Norbornan-2-ylpropan-2-one.

The fragrance composition according to the invention comprises or consists of 1-Norbornan-2-ylpropan-2-one and at least one further pleasant smelling compound different from 1-Norbornan-2-ylpropan-2-one. Preferably, the fragrance composition according to the invention comprises or consists of 1-Norbornan-2-ylpropan-2-one and two or more further pleasant smelling compounds different from 1-Norbornan-2-ylpropan-2-one. More preferably, the fragrance composition according to the invention comprises or consists of 1-Norbornan-2-ylpropan-2-one and three or more further pleasant smelling compounds different from 1-Norbornan-2-ylpropan-2-one. Most preferably, the fragrance composition according to the invention comprises or consists of 1-Norbornan-2-ylpropan-2-one and four or more further pleasant smelling compounds different from 1-Norbornan-2-ylpropan-2-one fragrances.

1-Norbornan-2-ylpropan-2-one according to the invention is usually used in a sensory effective amount, i.e. in a total amount in which it exerts a sensory effect.

Preferably, the weight ratio of 1-Norbornan-2-ylpropan-2-one to the total amount of pleasant smelling compounds different from 1-Norbornan-2-ylpropan-2-one is in the range of 1 to 1000 to 1 to 100, preferably from 1 to 600 to 1 to 400.

In a preferred embodiment according to the invention, 1-Norbornan-2-ylpropan-2-one is contained in the fragrance composition in a sensory effective amount sufficient to augment one or more pleasant olfactory impression of one or more pleasant smelling compounds different from 1-Norbornan-2-ylpropan-2-one, particularly for augmenting or improving the floweriness and/or naturalness, in particular more towards lavender, of one or more pleasant smelling compounds.

Examples of pleasant smelling compounds, in particular fragrances, which may advantageously be combined with 1-Norbornan-2-ylpropan-2-one in the context of the present invention can be found, for example, in S. Arctander, Perfume and Flavor Materials, Vol. I and II, Montclair, N. J. 1969, self-published, or K. Bauer et al., Common Fragrance and Flavor Materials, 4th Edition, Wiley-VCH, Weinheim 2001.

Specifically mentioned are: Extracts from natural raw materials such as essential oils, concretes, absolutes, resins, resinoids, balsams, tinctures such as.

Ambergris tincture; *Amyris* oil; *Angelica* seed oil; *Angelica* root oil; Anise oil; Valerian oil; Basil oil; tree moss absolute; bay oil; mugwort oil; benzoeresin; bergamot oil; Beeswax absolute; Birch tar oil; Bitter almond oil; Savory oil; *Bucco* leaf oil; *Cabreuva* oil; Cade oil; Calmus oil; Camphor oil; *Cananga* oil; Cardamom oil; *Cascarilla* oil; *Cassia* oil; Cassie-absolute; Castoreum-absolute; Cedar leaf oil; Cedarwood oil; *Cistus* oil; *Citronella* oil; Citron oil; *Copaiva* balsam; *Copaiva* balsam oil; Coriander oil; *Costus* root oil; Cumin oil; Cypress oil; *Davana* oil; Dill herb oil; Dill seed oil; Eau de brouts-Absolute; Oak moss absolute; Elemi oil; Tarragon oil; *Eucalyptus citriodora* oil; *Eucalyptus* oil; Fennel oil; Spruce needle oil; *Galbanum* oil; *Galbanum* resin; Geranium oil; Grapefruit oil; Guaiac wood oil; Gurjun balsam; Gurjun balsam oil; Helichrysum absolute; Helichrysum oil; Ginger oil; Iris root absolute; Iris root oil; Jasmine absolute; *Calamus* oil; Chamomile oil blue; Chamomile oil roman; Carrot seed oil; *Cascarilla* oil; Pine needle oil; Spearmint oil; Caraway oil; labdanum oil; labdanum absolute; labdanum resin; lavandin absolute; Lavandin oil; Lavender absolute; Lavender oil; Lemongrass oil; Lovage oil; Lime oil distilled; Lime oil pressed; Linaloe oil; *Litsea cubeba* oil; Bay leaf oil; Mace oil; Marjoram oil; Mandarin oil; Massoir bark oil; *Mimosa* absolute; Musk grain oil; Musk tincture; Muscat sage oil; Nutmeg oil; Myrrh absolute; Myrrh oil; Myrtle oil; Clove leaf oil; Clove flower oil; Neroli oil; Olibanum absolute; Olibanum oil; *Opopanax* oil; orange blossom absolute; orange oil; origanum oil;

palmarosa oil; patchouli oil; *Perilla* oil; Perubalsam oil; Parsley leaf oil; Parsley seed oil; Petitgrain oil; Peppermint oil; Pepper oil; Allspice oil; Pine oil; Poley oil; Rose absolute; Rosewood oil; Rose oil; Rosemary oil; Sage oil Dalmatian; Sage oil Spanish; Sandalwood oil; Celery seed oil; Spicy lavender oil; Star anise oil; *Styrax* oil; *Tagetes* oil; Fir needle oil; Tea tree oil; Turpentine oil; Thyme oil; Tolu balsam; Tonka absolute; tuberose-absolute; vanilla extract; violet leaf-absolute; verbena oil; vetiver oil; juniper berry oil; wine yeast oil; wormwood oil; wintergreen oil; ylang oil; hyssop oil; civet-absolute; cinnamon leaf oil; cinnamon bark oil and fractions thereof, or Ingredients isolated therefrom;

Individual odorants from the group of hydrocarbons, such as 3-carene; α-pinene; ß-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

of the aliphatic alcohols such as Hexanol; octanol; 3-octanol; 2,6-dimethylheptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of aliphatic aldehydes and their acetals, such as Hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6, 10-trimethyl-9-undecenal; 2,6,10-trimethyl-5,9-undecadienal; heptanaldiethyl acetal; 1,1-dimethoxy-2,2,5-trimethyl-4-hexene; citronellyloxyacetaldehyde; 1-(1-methoxy-propoxy)-(E/Z)-3-hexene;

of aliphatic ketones and their oximes such as 2-heptanone; 2-octanone; 3-octanone; 2-nonanone; 5-methyl-3-heptanone; 5-methyl-3-heptanone oxime; 2,4,4,7-tetramethyl-6-octen-3-on; 6-methyl-5-hepten-2-one;

of aliphatic sulfur-containing compounds such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

of aliphatic nitriles such as 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids, e.g. (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; Octyl acetate; 3-octyl acetate; 1-octene-3-yl acetate; ethyl butyrate; butyl butyrate; isoamyl butyrate; hexyl butyrate; (E)- and (Z)-3-hexenyl isobutyrate; Hexyl crotonate; ethyl isovalerate; ethyl 2-methylpentanoate; ethyl hexanoate; allyl hexanoate; ethyl heptanoate; allyl heptanoate; ethyl octanoate; Ethyl (E,Z)-2,4-decadienoate; methyl 2-octinate; methyl 2-noninate; allyl 2-isoamyloxyacetate; M ethy 1-3,7-dimethyl-2,6-octadiene-oate; 4-methyl-2-pentyl crotonate;

of acyclic terpene alcohols such as. Geraniol; nerol; lavadulol; nerolidol; farnesol; tetrahydrolinalool; tetrahydrogeraniol; 2,2-Dimethyl-3-(3-methylphenyl)propan-1-ol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-Dimethyloct-6-en-1-ol; (2E)-3,7-Dimethylocta-2,6-dien-1-ol; 3,7-dimethyl-1,5,7-octatrien-3-ol 2,6-dimethyl-2,5J-octatrien-1-ol; and their formates, acetates, propionates, isobutyrates, butyrates, isovalerianates, pentanoates, hexanoates, crotonates, tiglinates and 3-methyl-2-butenoates;

of the acyclic terpene aldehydes and ketones such as citronellal; 7-methoxy-3,7-dimethyloctanal; 2,6,10-trimethyl-9-undecenal; geranylacetone; and the dimethyl and diethylacetals of geranial, neral, of cyclic terpene alcohols such as. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiaol; and their formates, acetates, propionates, isobutyrates, butyrates, isovalerianates, pentanoates, hexanoates, crotonates, tiglinates and 3-methyl-2-butenoates;

of cyclic terpene aldehydes and ketones such as Menthone; isomenthone; 8-mercaptomenthan-3-on; carvone; camphor; fenchone; alpha-Ionone; beta-Ionone; alpha-n-methylionone; beta-n-methylionone; alpha-Isomethylionone; beta-Isomethyl-ionone; alpha-irone; beta-damascenone; 1-(2,4,4-trimethyl-2-cyclohexen-1-yl)-2-buten-1-one; 1,3,4,6,7,8a-Hexahydro-1,1,5,5-tetramethyl-2H-2,4a-methano-naphthalen-8 (5H)-on; 2-Methyl-4-(2,6,6-trimethyl-1-cyclohexen-1-yl)-2-butenal; Nootkatone; dihydronootkatone; 4,6,8-megastigmatriene-3-on; alpha-sinensal; beta-sinensal; acetylated cedarwood oil (methylcedrylketone);

of cyclic alcohols such as 4-tert-butylcyclohexanol; 3,3,5-trimethylcyclohexanol; 3-Isocamphylcyclohexanol; 2,6,9-trimethyl-Z2,Z5,E9-cyclododecatrien-1-ol; 2-Isobutyl-4-m ethyltetrahydro-2H-pyran-4-ol; 4-cyclohexylbutan-2-ol;

of cycloaliphatic alcohols such as. alpha,3,3-trimethylcyclohexylmethanol; 1-(4-Isopropylcyclohexyl) ethanol; 2-methyl-4-(2,2,3-trimethyl-3-cyclopent-1-yl) butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-Methyl-5-(2,2,3-trimethyl-3-cyclopent-1-yl)-4-penten-2-ol; 3,3-Dimethyl-5-(2,2,3-trimethyl-3-cyclopent-1-yl)-4-penten-2-ol; 1-(2,2,6-Trimethylcyclohexyl) pentan-3-ol; 1-(2,2,6-Trimethylcyclohexyl) hexan-3-ol;

cyclic and cycloaliphatic ethers, e.g. Cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyldodecahydro-naphtho[2,1-b]furan; 3a-ethyl-6,6,9a-trimethyldodecahydronaphtho[2,1 b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methyl propyl)-1,3-dioxane;

of cyclic and macrocyclic ketones such as 4-tert.-butylcyclohexanone; 2,2,5-trimethyl-5-pentylcyclopentanone; 2-heptylcyclopentanone; 2-pentyl-cyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopenta-decanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4 (5H)-indanone; 8-cyclohexadecen-1-one; 9-cycloheptadecen-1-on; cyclopentadecanone; cyclohexadecanone;

of cycloaliphatic aldehydes such as 2-methyl-4-(2,2,6-trimethyl-cyclohexen-1-yl)-2-butenal; 4-(4-hydroxy-4- methylpentyl)-3-cyclohexenecarbaldehyde; 4-(4-methyl-3-penten-1-yl)-3-cyclohexenecarbaldehyde;

of cycloaliphatic ketones, e.g. 1-(3,3-Dimethylcyclohexyl)-4-penten-1-on; 2,2-Dimethyl-1-(2,4-dimethyl-3-cyclohexen-1-yl)-1-propanon; 1-(5,5-Dimethyl-1-cyclohexen-1-yl)-4-penten-1-on; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert.-butyl-(2,4-dimethyl-3-cyclohexen-1-yl) ketone;

of ester of cyclic alcohols such as 2-tert-butylcyclohexyl acetate; 4-tert-butylcyclohexyl acetate; 2-tert-pentylcyclohexyl acetate; 4-tert-pentylcyclohexyl acetate; 3,3, 5-tri methylcyclohexyl acetate; decahydro-2-naphthyl acetate; 2-cyclo-pentylcyclopentyl crotonate; 3-pentyl tetrahydro-2H-pyran-4-yl acetate; decahydro-2,5,5,8a-tetramethyl-2-naphthyl acetate; 4,7-methano-3a,4,5,6, 7,7a-hexa-hydro-5, resp. 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

of esters of cycloaliphatic alcohols such as 1-cyclohexylethyl crotonate;

of esters of cycloaliphatic carboxylic acids, e.g. Allyl 3-cyclohexyl propionate; allyl cyclohexyloxy acetate; ice and trans-methyl dihydrojasmonate; ice and trans-methyl jasmonate; methyl 2-hexyl-3-oxocyclopentane carboxylate; ethyl 2-ethyl-6,6-dimethyl-2-cyclohexene carboxylate; ethyl 2,3,6,6-tetramethyl-2-cyclohexene carboxylate; ethyl 2-methyl-1,3-dioxolane-2-acetate;

of araliphatic alcohols such as Benzyl alcohol; 2-phenylethanol; 1-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-Isopropylphenyl) ethanol;

of esters of araliphatic alcohols and aliphatic carboxylic acids, e.g. Benzyl acetate; benzyl propionate; benzyl isobutyrate; benzyl isovalerate; 2-phenylethyl acetate; 2-phenylethyl propionate; 2-phenylethyl isobutyrate; 2-phenyl ethyl isovalerate; 1-phenylethyl acetate; alpha-trichloromethyl benzyl acetate; alpha, alpha-dimethylphenyl ethyl acetate; alpha, alpha-dimethylphenyl ethyl butyrate; cinnamyl acetate; 2-phenoxyethyl isobutyrate; 4-methoxybenzyl acetate;

of araliphatic ethers such as. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin; of aromatic and araliphatic aldehydes such as. e.g., benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-isobutylphenyl)propanal; 3-(4-tert. butyl-phenyl) propanal; cinnamaldehyde; alpha-butylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones such as acetophenone; 4-methylacetophenone; 4-methoxyacetophenone; 4-tert.-butyl-2,6-dimethylaceto-phenone; 4-phenyl-2-butanone; 4-(4-hydroxyphenyl)-2-butanone; 1-(2-naphtha-lenyl)ethanone; 2-benzofuranylethanone; (3-methyl-2-benzofuranyl)ethanone; benzophenone; 1,1,2,3,6-hexamethyl-5-indanyl methyl ketone; 6-tert-.butyl-1,1-di-methyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-aceto-naphthone;

of aromatic and araliphatic carboxylic acids and their esters, e.g. Benzoic acid; phenylacetic acid; methyl benzoate; ethyl benzoate; hexyl benzoate; benzyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cinnamate; allyl phenoxy acetate; methyl salicylate; hexyl salicylate; cyclohexyl salicylate; cis-3-hexenyl salicylate; benzyl salicylate; phenyl ethyl salicylate; methyl 2,4-dihydroxy-3,6-dimethylbenzoate; ethyl 3-phenyl glycidate; ethyl 3-methyl-3-phenyl glycidate;

of heterocyclic compounds such as 2,5-dimethyl-4-hydroxy-2H-furan-3-one; 2-ethyl-4-hydroxy-5-methyl-2H-furan-3-on; 3-hydroxy-2-methyl-4H-pyran-4-one; 2-ethyl-3-hydroxy-4H-pyran-4-one;

of lactones such as. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadecanolide; 9-hexadecene-1,16-olide; 10-oxa-1,16-hexadecanolide; 11-oxa-1,16-hexa-decanolide; 12-oxa-1,16-hexadecanolide; ethylene-1,12-dodecanedioate; ethylene-1,13-tridecanedioate; 2,3-dihydrocoumarin; octahydrocoumarin.

In a further preferred embodiment of the invention, 1-Norbornan-2-ylpropan-2-one is preferably combined with one or more, particularly preferably with two, three, four, five or more pleasant smelling compounds.

1-Norbornan-2-ylpropan-2-one to be used according to the invention advantageously (at least partially) achieves an odor enhancement of the pleasant-smelling olfactory impressions.

Preferably, said one, more or all pleasant smelling compounds different from 1-Norbornan-2-ylpropan-2-one are selected from the group consisting of fragrances having a molar mass within the range of from 150 g/mol to 285 g/mol, particularly alcohols, aldehydes, ketones, ethers, esters and carboxylates having a molar mass in the range of from 150 g/mol to 285 g/mol.

In a further preferred embodiment according to the invention, said one, more or all pleasant smelling compounds are selected from the group consisting of 4-Methoxybenzaldehyde, Borneol, Isoborneol, 1-benzopyran-2-one, 2-Ethyl-3-hydroxy-4H-pyran-4-one, 3-Ethoxy-4-hydroxybenzaldehyde, 1,3,3-Trimethyl-2-oxabicyclo[2.2.2]octane, methyl 2,4-dihydroxy-3,6-dimethylbenzoate, trans-3,7-dimethyl-2,7-octadien-1-ol, Geraniol acetate, cis-3-Hexenylisovalerianat, hexyl acetate, hexyl butyrate, hexyl isobutyrate, 2-methyl-2-butenoic acid, hexyl ester, Bornan-2-on, lavandin, 3,7-Dimethylocta-1,6-dien-3-ol, 5-Methyl-2-(propan-2-yl)cyclohexan-1-ol, (2Z)-3,7-Dimethylocta-2,6-dien-1-ol, Nerol acetate, α: (3E)-3,7-Dimethylocta-1,3,7-triene, cis-β: (3Z)-3,7-Dimethylocta-1,3,6-triene, trans-β: (3E)-3,7-Dimethylocta-1,3,6-triene, 4-Methyl-1-(propan-2-yl)cyclohex-3-en-1-ol, p-Menth-1-en-8-ol, 2-(4-Methylcyclohex-3-en-1-yl)propan-2-ol, 4-Hydroxy-3-methoxybenzaldehyde.

Preferably, 1-Norbornan-2-ylpropan-2-one is combined with one or more, particularly preferably with two, three, four, five or more of those preferred pleasant smelling compounds.

Perfume oil compositions containing 4-cyclohexyl-2-butanol are advantageously used for perfuming in liquid form, undiluted or diluted with a solvent. Suitable solvents for this are e.g. Ethanol, isopropanol, diethylene glycol monoethyl ether, glycerin, propylene glycol, 1,2-butylene glycol, dipropylene glycol, diethyl phthalate, triethyl citrate, isopropyimyristate etc.

Furthermore, fragrance compositions according to the invention can be adsorbed on a carrier, which ensures both a fine distribution of the fragrances in the product and a controlled release during use. Such carriers can be porous inorganic materials such as light sulfate, silica gels, zeolites, plasters, clays, clay granules, aerated concrete, etc. or organic materials such as wood, cellulose-based substances, sugar, dextrins (e.g. maltodextrin) or plastics such as PVC, polyvinyl acetates or polyurethanes. The resulting combination of compositions according to the invention and carrier substance is also to be understood as a fragrance composition according to the invention.

Fragrance compositions according to the invention can also be microencapsulated, spray-dried, as inclusion complexes or as extrusion products and added in this form to a product to be perfumed, for example.

If necessary, the properties of the compositions modified in this way can be further optimized by so-called "coating" with suitable materials with a view to a more targeted release of fragrances, for which purpose waxy plastics such as polyvinyl alcohol are preferably used. The resulting products in turn represent articles according to the invention.

Preferably, the amount of 1-Norbornan-2-ylpropan-2-one is in the range of 0.01 to 50% by weight, based on the total weight of the fragrance composition. More preferably, the amount of 1-Norbornan-2-ylpropan-2-one is in the range of 0.01 to 10% by weight, based on the total weight of the fragrance composition. More preferably, the amount of 1-Norbornan-2-ylpropan-2-one is in the range of 0.1 to 2.5% by weight, based on the total weight of the fragrance composition.

Fragrance compositions according to the invention can advantageously be used in concentrated form, in solutions or in the modified form described above for the production of perfumed articles according to the invention, such as. B. perfume extracts, eau de perfumes, eau de toilettes, aftershave, eau de colognes, pre-shave products, splash colognes and perfumed refreshing towels and the perfuming of acidic, alkaline and neutral cleaning agents such as floor cleaners, window glass cleaners, dishwashing detergents, Bathroom and sanitary cleaners, scouring milk, solid and liquid toilet cleaners, powder and foam carpet cleaners, textile fresheners, ironing aids, liquid detergents, powder detergents, laundry pretreatment agents such as bleaches, soaking agents and stain removers, fabric softeners, laundry soaps, washing tablets, and disinfectants Air fresheners in liquid, gel-like or applied form on a solid carrier, aerosol sprays, waxes and polishes such as furniture polishes, floor waxes, shoe creams and personal care products such as solid and liquid soaps, shower gels, shampoos, shaving soaps, shaving foams s, bath oils, cosmetic emulsions of the oil-in-water, of the water-in-oil and of the water-in-oil-in-water type such as, for example, skin creams and lotions, face creams and lotions, sun protection creams and lotions, after-sun creams and lotions, hand creams and lotions, foot creams and lotions, depilatory creams and lotions, after-shave creams and lotions, tanning creams and lotions, hair care products such as hair sprays, hair gels, setting hair lotions, Hair conditioners, permanent and semi-permanent hair dyes, hair shaping agents such as cold waves and hair straighteners, hair lotions, hair creams and lotions, deodorants and antiperspirants such as underarm sprays, roll-ons, deodorant sticks, deodorant creams, products in decorative cosmetics such as eye shadow, nail varnish, Lipsticks, mascara and candles, lamp oils, incense sticks, insecticides, repellants and fuels.

Of course, fragrance compositions according to the invention can also be included in cosmetic compositions or household compositions.

A further aspect of the present invention relates to a perfumed product comprising a fragrance composition as described above in a sensorial working amount, wherein the amount of said fragrance composition calculated on the total mass of the product preferably ranges from 0.01 to 10 wt.-%, more preferably from 0.1 to 5 wt.-%, and most preferably from 0.25 to 3 wt.-%.

In a preferred embodiment the perfumed product is selected from cosmetic, hygiene and/or household articles. Further preferred embodiments listed above also apply to the perfumed product of the present invention.

Preferably, the perfumed product is selected from the group consisting of detergents and cleaning agents, hygiene or care products, preferably in the field of body and hair care, cosmetics and household, preferably from the group consisting of perfume extracts, Eau de perfumes, eau de toilets, aftershave lotions, eau de colognes, pre-shave products, splash colognes, perfumed refreshing tissues, acidic, alkaline or neutral cleaning agents, textile fresheners, ironing aids, liquid detergents, powder detergents, laundry pretreatment agents, fabric softeners, Wash tablets, disinfectants, surface disinfectants, air fresheners, aerosol sprays, waxes and polishes, personal care products, hand creams and lotions, foot creams and lotions, depilatory creams and lotions, after shave creams and lotions, tanning creams and lotions, hair care products, hair care products, Products of the decorative cosmetics, candles, lamp oils, incense sticks, insecticides, repellants and fuels. Most preferably, the perfumed product is selected from alcoholic perfume, a personal hygiene product or a cleaning or care product for use in the home.

In addition, it is preferred for the perfumed product according to the invention that 1-Norbornan-2-ylpropan-2-one is contained in a sensory effective amount which is sufficient for a consumer to have one or more olfactory properties selected from the group consisting of more naturalness and/or an enhanced floral note.

The additives, auxiliaries and/or active substances described above are preferably not odoriferous substances. These can be, for example, preservatives, antibacterial agents, chelating agents, cleaning agents, emulsifiers, fats, etc. and in principle all substances that are used as additives, auxiliaries and/or active ingredients in cosmetics, especially in fragrance compositions, as well as in household compositions.

Another aspect of the invention relates to a method for augmenting of one or more pleasant olfactory impression of one or more pleasant smelling compounds, particularly for augmentation and/or improvement of the floweriness and/or naturalness, in particular more towards lavender, of one or more pleasant smelling compounds, wherein said compounds are different from 1-Norbornan-2-ylpropan-2-one, comprising or consisting of the following steps:

mixing the pleasant smelling compound with 1-Norbornan-2-ylpropan-2-one, wherein the amount of 1-Norbornan-2-ylpropan-2-one is sufficient for augmentation and/or improvement of the floweriness and/or naturalness of one or more pleasant smelling compounds.

Preferably, the weight ratio of 1-Norbornan-2-ylpropan-2-one to the total amount of pleasant smelling compounds different from 1-Norbornan-2-ylpropan-2-one is in the range of 1 to 1000 to 1 to 100, preferably from 1 to 600 to 1 to 400.

In a preferred embodiment according to the invention, the at least one pleasant smelling compound is selected from the group consisting of 4-Methoxybenzaldehyde, Borneol, Isoborneol, 1-benzopyran-2-one, 2-Ethyl-3-hydroxy-4H-pyran-4-one, 3-Ethoxy-4-hydroxybenzaldehyde, 1,3,3-Trimethyl-2-oxabicyclo[2.2.2]octane, methyl 2,4-dihydroxy-3,6-dimethylbenzoate, trans-3,7-dimethyl-2,7-octadien-1-ol, Geraniol acetate, cis-3-Hexenylisovalerianat, hexyl acetate, hexyl butyrate, hexyl isobutyrate, 2-methyl-2-butenoic acid, hexyl ester, Bornan-2-on, lavandin, 3,7-Dimethylocta-1,6-dien-3-ol, 5-Methyl-2-(propan-2-yl)cyclohexan-1-ol, (2Z)-3,7-Dimethylocta-2,6-dien-1-ol, Nerol acetate, a: (3E)-3,7-Dimethylocta-1,3,7-triene, cis-β: (3Z)-3,7-Dimethylocta-1,3,6-triene, trans-β: (3E)-3,7-Dimethylocta-1,3,6-triene, 4-Methyl-1-(propan-2-yl)cyclohex-3-en-1-ol, p-Menth-1-en-8-ol, 2-(4-Methylcyclohex-3-en-1-yl)propan-2-ol, 4-Hydroxy-3-methoxybenzaldehyde.

Preferably, 1-Norbornan-2-ylpropan-2-one is combined with one or more, particularly preferably with two, three, four, five or more of those preferred pleasant smelling compounds, in particular fragrances.

Further preferred embodiments listed above also apply to method of the present invention.

In the following, the invention is further characterized on the basis of the examples.

EXAMPLES

Example 1: Synthesis of 1-Norbornan-2-ylpropan-2-one 84 g (0.89 mol) of 2-norbornene, 2329 g (17.9 mol) of acetoacetic ester and 24 g (0.16 mol) of di-tert-butyl peroxide were placed in a 5 liter autoclave and heated under a nitrogen pressure of 5 bar. The mixture was stirred at 155-160° C. for one hour. The pressure rose to 11 bar. The mixture was quickly cooled to room temperature and then evaporated on a rotary evaporator at 60-70° C. and 10-5 mbar. The residue was fractionated on a 5 cm column with Raschig rings. The product was distilled at a top temperature of 53-99° C. and a vacuum of 0.5 mbar. 97 g of ethyl 2-norbornan-2-yl-3-oxo-butanoate according to Formula II with a GC content of 86% (2 stereoisomers in the ratio of 3.5:6.5) were obtained.

Formula II

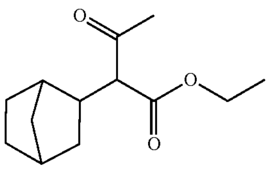

1H NMR: (400 MHZ, CDCl3) δ 4.26-4.09 (m, 4H), 3.20 (d, J=11.7 Hz, 1H), 3.17 (d, J=11.7 Hz, 1H), 2.27-2.16 (m, 4H), 2.23 (s, 3H), 2.19 (s, 3H), 2.02-1.96 (m, 1H), 1.90-1.74 (m, 1H), 1.59-1.41 (m, 6H), 1.35-1.24 (m, 4H), 1.28 (t, J=7.2 Hz, 3H), 1.25 (t, J=7.1 Hz, 3H), 1.22-1.16 (m, 2H), 1.14 (dddd, J=11.0, 5.3, 2.5, 1.1 Hz, 2H), 1.09 (ddd, J=9.2, 4.2, 2.7 Hz, 1H), 1.02-0.92 (m, 1H)

Peak 1 (NK) m/z: 43 (70), 55 (14), 66 (51), 79 (28), 94 (48), 108 (16), 130 (100), 136 (37), 153 (9), 182 (30)

Peak 2 (HK) m/z: 43 (100), 55 (19), 67 (66), 79 (41), 94 (72), 108 (29), 130 (61), 136 (78), 153 (17), 182 (99)

100 g (0.35 mol) of 79% ethyl 2-norbornan-2-yl-3-oxobutanoate were placed in a 500 ml stirrer with contact thermometer, 10 cm Vigreux column, distillation bridge, dropping funnel and heating hood and heated to 200° C. At this temperature, 20 ml of water were added dropwise over the course of 90 minutes, with parallel removal of the distillate. The residue was distilled on the same apparatus. The product was distilled at a top temperature of 73-90° C. and a vacuum of 5 mbar. 58 g of 1-norbornan-2-ylpropan-2-one according to Formula I with a GC content of 90% were obtained.

Formula I

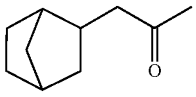

1H NMR: (400 MHZ, CDCl3) δ 2.42 (dd, J=16.2, 7.4 Hz, 1H), 2.26 (dd, J=16.2, 7.7 Hz, 1H), 2.22-2.18 (m, 1H), 2.11 (s, 2H), 1.94-1.90 (m, 1H), 1.90-1.85 (m, 1H), 1.56-1.50 (m, 1H), 1.50-1.41 (m, 2H), 1.31-1.25 (m, 1H), 1.25-1.20 (m, 1H), 1.17-1.13 (m, 1H), 1.12-1.07 (m, 1H), 0.99 (dtd, J=12.0, 4.5, 2.6 Hz, 1H).

m/z: 43 (100), 58 (20), 66 (75), 79 (26), 83 (33), 94 (59), 109 (24), 119 (7), 134 (17), 152 (6)

Example 2: Fragrance Composition

All amounts are given in weight percent.

TABLE 1

Example of a fragrance composition according to the invention

| | |
|---|---|
| ANISALDEHYD REIN | 1 |
| BORNEOL L/ISOBORNEOL 65/35 | 20 |
| CUMARIN | 2 |
| DIPROPYLENGLYCOL | 106.5 |
| ETHYLMALTOL | 4.5 |
| ETHYLVANILLIN | 3 |
| EUCALYPTOL NAT. | 40 |
| EVERNYL | 8 |
| GERANIOL SUPRA | 20 |
| GERANYLACETAT PUR | 15 |
| HEXENYLISOVALERIANAT CIS-3 10% IPM | 3 |
| HEXYLACETAT | 1.5 |
| HEXYLBUTYRAT | 2.5 |
| HEXYLISOBUTYRAT | 1.5 |
| HEXYLTIGLINAT | 1 |
| KAMPFER DL | 34 |
| KRAUSEMINZOEL 65% AMERIK. 10% DPG | 6 |
| LAVANDIN ESPIEUR CENSO | 150 |
| LINALOOL | 330 |
| MENTHOL L KOMPAKTIERT | 1.5 |
| MYRTENOEL | 10 |
| NEROL 900 | 6 |
| NERYLACETAT | 10 |
| OCIMEN | 15 |

TABLE 1-continued

| Example of a fragrance composition according to the invention | |
|---|---|
| ORANGENOEL | 45 |
| TEEBAUMOEL | 100 |
| TERPINENOL-4 NAT. | 15 |
| TERPINEOL REIN | 45 |
| VANILLIN | 3 |

According to an expert panel, after the addition of 2% 1-Norbornan-2-ylpropan-2-one the composition smells much more floral and natural, more towards lavender.

The invention claimed is:

1. A method for augmenting of one or more pleasant olfactory impression of at least one pleasant smelling compound wherein said at least one pleasant smelling compound is different from 1-Norbornan-2-ylpropan-2-one, the method comprising or consisting of the following steps:

mixing the at least one pleasant smelling compound with 1-Norbornan-2-ylpropan-2-one, wherein the amount of 1-Norbornan-2-ylpropan-2-one is sufficient for augmenting and/or improving of the floweriness and/or naturalness of the at least one pleasant smelling compound.

2. The method according to claim 1, wherein at least one pleasant smelling compound different from 1-Norbornan-2-ylpropan-2-one is selected from the group consisting of fragrances having a molar mass within the range of from 150 g/mol to 285 g/mol, particularly alcohols, aldehydes, ketones, ethers, esters and carboxylates having a molar mass in the range of from 150 g/mol to 285 g/mol.

3. The method according to claim 1, wherein said at least one pleasant smelling compound is selected from the group consisting of 4-Methoxybenzaldehyde, Borneol, Isoborneol, 1-benzopyran-2-one, 2-Ethyl-3-hydroxy-4H-pyran-4-one, 3-Ethoxy-4-hydroxybenzaldehyde, 1,3,3-Trimethyl-2-oxabicyclo[2.2.2]octane, methyl 2,4-dihydroxy-3,6-dimethylbenzoate, trans-3,7-dimethyl-2,7-octadien-1-ol, Geraniol acetate, cis-3-Hexenylisovalerianat, hexyl acetate, hexyl butyrate, hexyl isobutyrate, 2-methyl-2-butenoic acid, hexyl ester, Bornan-2-on, lavandin, 3,7-Dimethylocta-1,6-dien-3-ol, 5-Methyl-2-(propan-2-yl)cyclohexan-1-ol, (2Z)-3,7-Dimethylocta-2,6-dien-1-ol, Nerol acetate, α: (3E)-3,7-Dimethylocta-1,3,7-triene, cis-β: (3Z)-3,7-Dimethylocta-1,3,6-triene, trans-β: (3E)-3,7-Dimethylocta-1,3,6-triene, 4-Methyl-1-(propan-2-yl)cyclohex-3-en-1-ol, p-Menth-1-en-8-ol, 2-(4-Methylcyclohex-3-en-1-yl)propan-2-ol, and 4-Hydroxy-3-methoxybenzaldehyde.

4. The method according to claim 1, wherein the ratio of total mass of the at least one pleasant smelling compound to the total mass of 1-Norbornan-2-ylpropan-2-one is in the range of 1 to 1000 to 1 to 100.

5. A fragrance composition comprising or consisting of 1-Norbornan-2-ylpropan-2-one and at least one further pleasant smelling compound different from 1-Norbornan-2-ylpropan-2-one.

6. The fragrance composition according to claim 5, wherein the weight ratio of 1-Norbornan-2-ylpropan-2-one to the total amount of the at least one pleasant smelling compound different from 1-Norbornan-2-ylpropan-2-one is in the range of 1 to 1000 to 1 to 100.

7. The fragrance composition according to claim 5, wherein the amount of 1-Norbornan-2-ylpropan-2-one is sufficient to augment one or more pleasant olfactory impression of the at least one pleasant smelling compound different from 1-Norbornan-2-ylpropan-2-one, wherein the one or more pleasant olfactory impression optionally comprises floweriness and/or naturalness of the at least one pleasant smelling compound.

8. The fragrance composition according to claim 5, wherein the amount of 1-Norbornan-2-ylpropan-2-one is in the range of 0.01 to 50% by weight, based on the total weight of the fragrance composition.

9. The fragrance composition according to claim 5, wherein the amount of 1-Norbornan-2-ylpropan-2-one is in the range of 0.01 to 10% by weight, based on the total weight of the fragrance composition.

10. The fragrance composition according to claim 5, wherein the at least one pleasant smelling compound is selected from the group consisting of 4-Methoxybenzaldehyde, Borneol, Isoborneol, 1-benzopyran-2-one, 2-Ethyl-3-hydroxy-4H-pyran-4-one, 3-Ethoxy-4-hydroxybenzaldehyde, 1,3,3-Trimethyl-2-oxabicyclo[2.2.2]octane, methyl 2,4-dihydroxy-3,6-dimethylbenzoate, trans-3,7-dimethyl-2,7-octadien-1-ol, Geraniol acetate, cis-3-Hexenylisovalerianat, hexyl acetate, hexyl butyrate, hexyl isobutyrate, 2-methyl-2-butenoic acid, hexyl ester, Bornan-2-on, lavandin, 3,7-Dimethylocta-1,6-dien-3-ol, 5-Methyl-2-(propan-2-yl)cyclohexan-1-ol, (2Z)-3,7-Dimethylocta-2,6-dien-1-ol, Nerol acetate, α: (3E)-3,7-Dimethylocta-1,3,7-triene, cis-β: (3Z)-3,7-Dimethylocta-1,3,6-triene, trans-β: (3E)-3,7-Dimethylocta-1,3,6-triene, 4-Methyl-1-(propan-2-yl)cyclohex-3-en-1-ol, p-Menth-1-en-8-ol, 2-(4-Methylcyclohex-3-en-1-yl)propan-2-ol, and 4-Hydroxy-3-methoxybenzaldehyde.

11. A perfumed product comprising a fragrance composition according to claim 5 in a sensorial working amount, wherein the amount of said fragrance composition calculated on the total mass of the product ranges from 0.01 to 10 wt.-%, from 0.1 to 5 wt.-%, or from 0.25 to 3 wt.-%.

12. The perfumed product according to claim 11, wherein the product is selected from cosmetic, hygiene and/or household articles.

* * * * *